United States Patent
Zikov et al.

(10) Patent No.: US 7,672,717 B1
(45) Date of Patent: Mar. 2, 2010

(54) METHOD AND SYSTEM FOR THE DENOISING OF LARGE-AMPLITUDE ARTIFACTS IN ELECTROGRAMS USING TIME-FREQUENCY TRANSFORMS

(75) Inventors: Tatjana Zikov, Shaker Heights, OH (US); Stephane Bibian, Vancouver (CA); Guy Albert Dumont, Vancouver (CA); Mihai Huzmezan, Vancouver (CA); Craig Robert Ries, Vancouver (CA)

(73) Assignee: Bionova Technologies Inc., Vancouver, BC (CA)

( * ) Notice: Subject to any disclaimer, the term of this patent is extended or adjusted under 35 U.S.C. 154(b) by 1498 days.

(21) Appl. No.: 10/968,348

(22) Filed: Oct. 19, 2004

Related U.S. Application Data (60) Provisional application No. 60/512,863, filed on Oct. 22, 2003.

(51) Int. Cl.
*A61B 5/04* (2006.01)
*A61B 5/05* (2006.01)

(52) U.S. Cl. .................. 600/544; 600/509; 600/546; 600/547

(58) Field of Classification Search ............. 600/300, 600/544, 545, 508–526, 546, 547
See application file for complete search history.

(56) References Cited

U.S. PATENT DOCUMENTS

| | | | |
|---|---|---|---|
| 5,995,868 A * | 11/1999 | Dorfmeister et al. | 600/544 |
| 6,339,721 B1 * | 1/2002 | Yamazaki et al. | 600/544 |
| 6,549,804 B1 * | 4/2003 | Osorio et al. | 600/544 |
| 7,099,714 B2 * | 8/2006 | Houben | 600/509 |
| 2004/0010203 A1 * | 1/2004 | Bibian et al. | 600/544 |
| 2004/0111121 A1 * | 6/2004 | Brown et al. | 607/5 |
| 2004/0193065 A1 * | 9/2004 | Houben | 600/509 |
| 2004/0243017 A1 * | 12/2004 | Causevic | 600/544 |
| 2007/0032737 A1 * | 2/2007 | Causevic et al. | 600/544 |
| 2007/0038382 A1 * | 2/2007 | Keenan | 702/19 |

* cited by examiner

*Primary Examiner*—Charles A Marmor, II
*Assistant Examiner*—Navin Natnithithadha (57) ABSTRACT

The present invention relates to a method of signal processing of electrograms for use in medical devices, preferably by time-frequency transforms. The present invention additionally relates to a system for receiving and analyzing such signals. The present invention preferably is a method utilizing the time-frequency transforms, such as wavelet transforms, for the purpose of artifact removal from EGs. These transforms decompose a signal in both time and frequency domains, and therefore, are well suited for non-stationary signal analysis. As a result, dissimilar signal features are well localized both in time and frequency, which potentially provides a good separation between the signal of interest and artifacts. This particularly applies to large-amplitude artifacts corrupting EGs.

23 Claims, 11 Drawing Sheets

METHOD AND SYSTEM FOR THE DENOISING OF LARGE-AMPLITUDE ARTIFACTS IN ELECTROGRAMS USING TIME-FREQUENCY TRANSFORMS

CROSS REFERENCE TO RELATED APPLICATIONS

This application is a continuation-in-part of provisional patent application No. 60/512,863 filed Oct. 22, 2003.

BACKGROUND OF THE INVENTION

1. Field of the Invention

The present invention relates to a method of signal processing of electrograms for use in medical devices. The present invention additionally relates to a system for receiving and analyzing such signals.

2. Technical Background

Electrograms are a class of electrical signals, which are representations of underlying physiological processes. They are obtained through the medium of electrochemical, electromechanical or electrooptical sensors. Electrograms are particularly useful to monitor a patient's or subject's physiological state, diagnose illnesses and devise proper therapeutic strategies.

A particularity of this class of signals is their high sensitivity to environmental noise and other artifacts. Common artifacts are often of large amplitude as compared to the electrogram itself, which is typically a signal of rather small amplitude ($\mu V$ or mV). Contamination by artifacts can significantly reduce the diagnostic and therapeutic utility of an electrogram. Therefore, there is a profound need in the medical community for signal processing techniques that remove these artifacts from EGs prior to their interpretation.

One example of a widely used electrogram is the Electroencephalogram (EEG), a measure of electrical brain activity. The EEG signal provides researchers with a noninvasive insight into the intricacy of the human brain. It is a valuable tool for clinicians in numerous applications, from the diagnosis of neurological disorders, to the clinical monitoring of depth of anesthesia. For an awake healthy subject, the normal EEG amplitude is in the order of 20-50 $\mu V$, making this signal very susceptible to various artifacts, which cause problems for its analysis and interpretation. In current data acquisition, eye movement and blinks related artifacts, as well as other electrophysiological contaminating signals (e.g., heart and muscle activity, head and body movements), are often the most dominant artifacts. Eye movements and blinks produce a large electrical signal around the eyes (in the order of mV), known as Electrooculogram (EOG), which spreads across the scalp and contaminates the EEG. These contaminating potentials are commonly referred to as Ocular Artifacts (OAs). Another common large-amplitude artifact (in the order mV) in the EEG signal is Electrocardiogram (ECG), which originates from electrical activity of the heart. In addition, movement and muscle activity artifacts, commonly referred to as Electromyogram (EMG), can be of very large amplitude and contain high frequencies.

There have been many attempts to successfully remove artifacts and noise from EGs and other biosignals. However, this task has proven to be a constant challenge in the signal-processing field. The rejection of epochs contaminated with artifacts usually leads to a substantial loss of data. Asking subjects not to produce artifacts is often inappropriate or inadequate. In addition, the fact that a subject needs to concentrate on fulfilling these requirements might by itself influence the interpretation of the EG. In the past, significant efforts have been made among researchers to find a way to successfully remove large-amplitude artifacts from EGs. An appropriate example for prior attempts are the techniques for removal of OAs from the EEG signal.

For example, time-domain regression methods have been widely used for removal of OAs from the EEG. These techniques involve the subtraction of some portion of the recorded Electrooculogram (EOG) from the EEG. They assume that the propagation of ocular potentials is volume conducted, frequency independent and without any time delay. Others argued that the scalp is not a perfect volume conductor, and thus, attenuates some frequencies more than others. Consequently, frequency-domain regression was proposed. However, neither time nor frequency regression techniques take into account the propagation of the brain signals into the recorded EOG. Thus a portion of relevant EEG signal is always cancelled out along with the artifact. Moreover, regression techniques mainly use different correction coefficients for different type of artifacts, e.g., eye blinks versus eye movements. They also heavily depend on the regressing artifact channel, in this case EOG channel. Eventually, more sophisticated regression methods were proposed for simultaneous correction of different artifacts, e.g., blinks and eye movement artifacts. Also, the influence of the EEG-to-EOG propagation has been somewhat minimized by these methods.

In an attempt to overcome the problem of the EEG-to-EOG propagation, a multiple source eye correction method has been proposed. In this method, the OA was estimated based on the source eye activity rather than the EOG signal. The method involves obtaining an accurate estimate of the spatial distribution of the eye activity from calibration data, which is a rather difficult task. Due to its de-correlation efficiency, the principal component analysis (PCA) has been applied for OA removal from the multi-channel EEG and it outperformed the previously mentioned methods. However, it has been shown that PCA cannot fully separate OAs from the EEG when comparable amplitudes are encountered.

Recently, independent component analysis (ICA) has demonstrated a superior potential for the removal of a wide variety of artifacts from the EEG, even in a case of comparable amplitudes. ICA simultaneously and linearly unmixes multichannel scalp recordings into independent components, which are often physiologically plausible. Also, there is no need for a reference channel corresponding to each artifact source. However, ICA artifact removal is not yet fully automated and requires visual inspection of the independent components in order to decide of their removal.

Other attempts have applied different adaptive signal processing techniques. The performance of these methods also relies on minimal contamination of the EG of interest by the reference artifactual signal. These prior attempts have achieved only partial success because of being based on signal processing techniques which are not optimal for the analysis of a particular EG signal of interest. Electrograms such as the EEG are often characterized by their non-stationary nature, i.e., their time-frequency characteristics can significantly change over time. In addition, artifacts are often transitory in nature (i.e., localized in time), which cannot be captured by traditional spectral analysis. Therefore, it is natural to explore signal processing techniques that can capture these non-stationary events.

It is therefore an object of the present invention to develop a signal processing method utilizing time-frequency transforms, such as wavelet transforms, for the purpose of artifact removal from EGs. These transforms decompose a signal in both time and frequency domains, and therefore, are well suited for non-stationary signal analysis. As a result, dissimilar signal features are well localized both in time and frequency, which potentially provides a good separation between the signal of interest and artifacts. This particularly applies to large-amplitude artifacts corrupting EGs.

It is further an object of the present invention to use a method of signal analysis, which utilizes wavelet denoising. However, unlike in the present invention, conventional wavelet denoising is used for the removal of an additive white Gaussian noise (AWGN) or colored (i.e., correlated) noise from smooth and coherent signals, assuming a relatively high signal-to-noise ratio (SNR). In contrast to conventional denoising, the present invention applies to large-amplitude transient artifacts from not necessarily smooth, coherent or stationary signals (e.g., EEG).

It is still further an object of the present invention to utilize a method of an over-complete (i.e., redundant) time-frequency transform. Over-complete transforms yield more coefficients in each time-frequency span of the transform, which provides a better means for statistical analysis when deriving thresholds. Also, the resulting denoised signals are smoother, i.e., without introduced ringing artifacts.

SUMMARY OF THE INVENTION

The present invention relates to a method of signal processing of electrograms for use in medical devices, preferably by time-frequency transforms. The present invention additionally relates to a system for receiving and analyzing such signals.

The present invention preferably is a method utilizing the time-frequency transforms, such as wavelet transforms, for the purpose of artifact removal from EGs. These transforms decompose a signal in both time and frequency domains, and therefore, are well suited for non-stationary signal analysis. As a result, dissimilar signal features are well localized both in time and frequency, which potentially provides a good separation between the signal of interest and artifacts. This particularly applies to large-amplitude artifacts corrupting EGs. By these artifacts we assume artifactual signals having a significantly larger energy than the EG signal of interest in at least one of the resulting time-frequency spans of the chosen transform. Thus, the resulting coefficients in the transform domain will be significantly larger in case of artifactual signals than the artifact-free EG. For example, in case of EEG signals of interest, ocular and ECG artifacts will result in large, time-localized coefficients in the time-frequency spans corresponding to lower frequencies, while EMG artifacts typically produce large coefficients in those corresponding to higher frequencies. Consequently, by reducing the coefficients that exceed the pre-selected thresholds in the transform domain, and recomposing the signal by applying the inverse of a chosen transform, we can successfully remove large-amplitude artifacts from the EG signal. The technique is even more successful as the amplitude of a contaminating artifact increases.

Even more preferably, the present invention, preferably, relates to a wavelet based denoising technique for correction of the electrograms (EGs) in the presence of artifacts, and in particular, large-amplitude artifacts. One of the typical applications of wavelet denoising is the noise suppression, e.g., in audio or video signals. Wavelet denoising of signals corrupted by noise comprises of three steps: the application of wavelet transform, thresholding of the resulting wavelet coefficients, and the application of the inverse wavelet transform. However, unlike in the present invention, conventional wavelet denoising is used for the removal of an additive white Gaussian noise (AWGN) or colored (i.e., correlated) noise from smooth and coherent signals, assuming a relatively high signal-to-noise ratio (SNR). Smoothness of a signal is a property related to its bandwidth, and to how many times it can be differentiated. A coherence property is related to which degree the signal energy is being well concentrated in both the time and frequency domains. Coherent signals decompose into very few time-frequency domain coefficients that carry most of the signal energy. However, incoherent noise requires most of the resulting decomposition coefficients that span the entire time-frequency space in order to represent most of the noise energy. Therefore, unlike conventional denoising, the present invention applies to large-amplitude transient artifacts from not necessarily smooth, coherent or stationary signals (e.g., EEG). This fact results in one obvious difference in the implementation; the present invention reduces coefficients that exceed the pre-selected thresholds, while conventional denoising reduces those smaller than the thresholds. Another major difference is that conventional thresholds are calculated based on the estimate of the noise variance, while the present invention relies only on the statistical characteristics of the artifact-free EG signal of interest.

The method of the present invention, preferably, is based on an over-complete wavelet expansion of the EG using the Stationary Wavelet Transform (SWT), followed by the thresholding of the wavelet coefficients corrupted by the artifacts. Over-complete transforms yield more coefficients in each time-frequency span in transform domain, which offers a better means for deriving the thresholds, a better characterization of artifacts and smoother denoised signals. Therefore, the Stationary (also called Over-complete or Redundant) Wavelet Transform (SWT) is preferred; however any of the following can be used: Discrete Wavelet Transform, Wavelet Packet Transform, Over-complete Wavelet Packet Transform or any transform with joint time-frequency localization properties, such as Short-Time Fourier Transform and others.

The term thresholding in case of the present invention refers to reducing or setting to zero those coefficients that exceed the pre-calculated thresholds in different time-frequency spans of a chosen transform. Due to its low algorithmic complexity, this technique is suitable as a pre-processing stage in medical devices that use EG signals as the main source for extraction of relevant clinical information. It can also be used to present the denoised EG signals directly to the practitioner in order to facilitate their visual interpretation.

The present invention preferably results in a technique that has one or more of the following benefits that it can be fully automated; it does not require reference artifact channels; it can be applied to a single channel or multiple EG channels; it simultaneously removes a variety of artifacts; and it is of a low computational complexity and thus suitable for real-time implementation.

In one embodiment, the present invention includes a method for removing artifacts from an observed electrogram of a subject in order to provide a denoised electrogram without artifact, said method comprising acquiring a plurality of reference electrograms, each said reference electrogram being free of said artifacts; selecting a time-frequency transform which, when applied to said reference electrograms yields a plurality of reference coefficient sets, each said reference coefficient set corresponding to a respective time-frequency span; selecting for each time-frequency span a threshold; receiving an electrogram from said subject to produce said observed electrogram; applying said time-frequency transform to said observed electrogram to produce a plurality of observed coefficient sets, each said observed coefficient set corresponding to a respective time-frequency span; comparing each coefficient of each said observed coefficient set with the corresponding threshold for a respective time-frequency span; replacing each coefficient of each said observed coefficient set which exceeds the threshold for a respective time-frequency span with a replacement value in order to produce denoised observed coefficient sets; and applying the inverse transform of said selected time-frequency transform to said denoised observed coefficient sets to reconstruct the denoised electrogram.

In another embodiment, the present invention includes a system for receiving an electrogram and removing artifacts from an observed electrogram, said system comprising a sensor for receiving the electrogram of said subject to complement said database of reference electrograms, and for producing said observed electrogram; and a digital signal processor for applying said time-frequency transform to said reference electrograms to produce a plurality of reference coefficient sets, each said reference coefficient set corresponding to a respective time-frequency span; calculating a threshold for each said time-frequency span using a corresponding reference coefficient set; applying said time-frequency transform to said observed electrogram to produce a plurality of observed coefficient sets, each said observed coefficient set corresponding to a respective time-frequency span; comparing each coefficient of each said observed coefficient set with the corresponding threshold for a respective time-frequency span; replacing each coefficient of each said observed coefficient set which exceeds the threshold for a respective time-frequency span with a replacement value in order to produce denoised observed coefficient sets; and applying the inverse transform of said time-frequency transform to said denoised observed coefficient sets to reconstruct the denoised electrogram.

In still another embodiment, the present invention includes a computer program product for removing artifacts from an observed electrogram of a subject in order to produce a denoised electrogram without artifact, given a time-frequency transform, and given a database of reference electrograms, each said reference electrogram being free of said artifacts, and said computer program product comprising a computer usable medium having a computer readable program code embodied in said medium for classifying said observed electrogram as an artifact-free electrogram or an artifactual electrogram; appending said artifact-free electrogram into a database of reference electrograms; applying said time-frequency transform to said reference electrograms to produce a plurality of reference coefficient sets, each said reference coefficient set corresponding to a respective time-frequency span; calculating a threshold for each said time-frequency span using a corresponding reference coefficient set; applying said time-frequency transform to said observed electrogram to produce a plurality of observed coefficient sets, each said observed coefficient set corresponding to a respective time-frequency span; comparing each coefficient of each said observed coefficient set with the corresponding threshold for a respective time-frequency span; replacing each coefficient of each said observed coefficient set which exceeds the threshold for a respective time-frequency span with a replacement value in order to produce denoised observed coefficient sets; and applying the inverse transform of said time-frequency transform to said denoised observed coefficient sets to reconstruct the denoised electrogram.

In still another embodiment, the present invention includes a method for removing artifacts from an observed electrogram of a subject in order to provide a denoised electrogram without artifact, said method comprising acquiring a plurality of reference electrograms, each said reference electrogram being free of said artifacts; selecting a time-frequency transform which, when applied to said reference electrograms yields a plurality of reference coefficient sets, each said reference coefficient set corresponding to a respective time-frequency span; selecting for each time-frequency span a threshold; receiving an electrogram from said subject to produce said observed electrogram; applying said time-frequency transform to said observed electrogram to produce a plurality of observed coefficient sets, each said observed coefficient set corresponding to a respective time-frequency span; comparing each coefficient of each said observed coefficient set with the corresponding threshold for a respective time-frequency span; replacing each coefficient of each said observed coefficient set which is less than the threshold for a respective time-frequency span with a replacement value in order to produce artifactual observed coefficient sets; applying the inverse transform of said selected time-frequency transform to said artifactual observed coefficient sets to reconstruct the artifactual electrogram, and subtracting the artifactual electrogram from the observed electrogram in order to obtain the denoised electrogram.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

BRIEF DESCRIPTION OF THE DRAWINGS

FIG. 3.a) is a block diagram of stationary wavelet transform decomposition performed using filter banks; and b) is another graph showing dyadic tiling of a frequency space.

DESCRIPTION OF THE PREFERRED EMBODIMENT

The present invention relates to a method of signal processing of electrograms for use in medical devices, preferably by time-frequency transforms. The present invention additionally relates to a system for receiving and analyzing such signals.

The denoising method of the present invention provides the means for removing contaminating artifacts from the observed EG. This technique is illustrated in one embodiment, for the removal of Ocular Artifacts (OAs) from the Electroencephalogram (EEG) in conscious subjects. However, the same technique can also be used to remove a variety of large-amplitude artifacts such as the heart artifacts, and/or muscle and movement artifacts, from a variety of EG signals.

Figure 2:
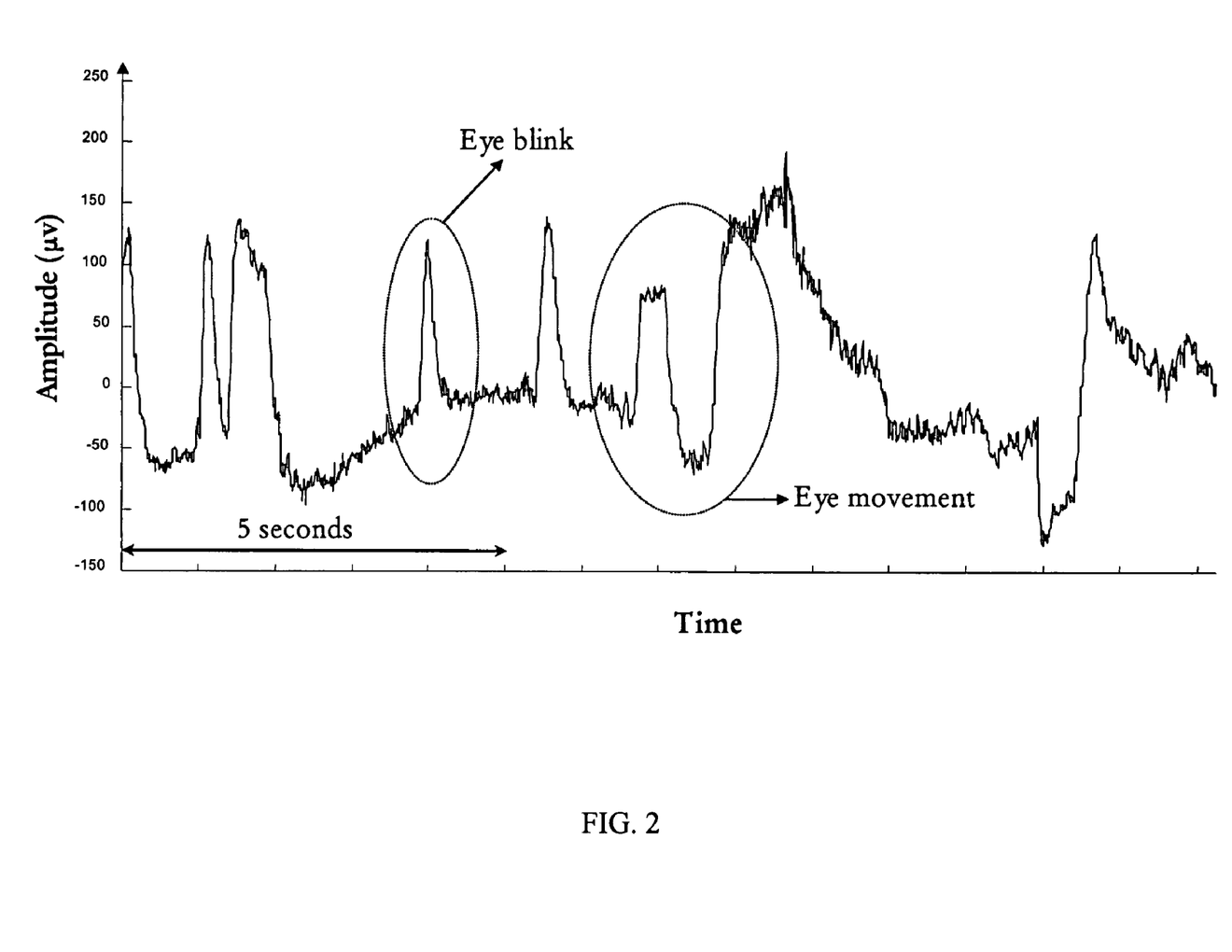
FIG. 2 is a graph showing an EEG signal with artifacts embedded within the signal.

The present invention relies on the time-frequency decomposition of the observed electrogram. For illustration purposes, consider another embodiment of a single-channel electroencephalogram. EEG signals are representative of the cortical activity of a subject and can be used in a large variety of medical applications. FIG. 2 is a graph showing an EEG signal with artifacts embedded within the signal. FIG. 2 demonstrates that normal EEG signals are in the range of a few tens of $\mu V$, and are very sensitive to a variety of artifacts, and in particular, ocular movements and eye blinks. These EEG signals are also very sensitive to muscle\movement and heart activity artifacts, and environmental noise.

Figure 4:
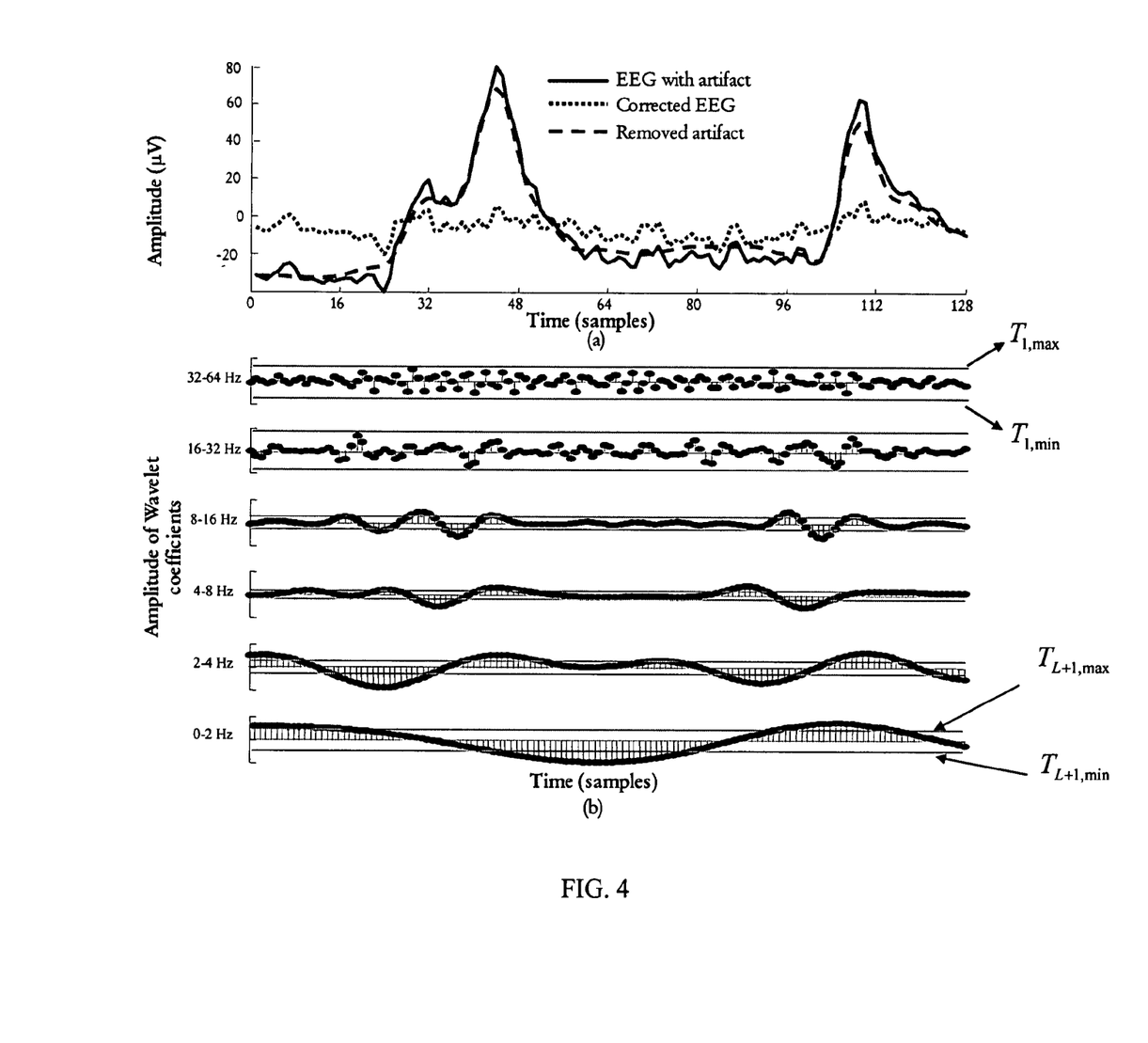
FIG. 4 is a graph showing an EEG signal time series corrupted by artifacts and broken down into coefficients of different time-frequency spans.

Another embodiment of the denoising method can be used to analyze one of the most common sources of EEG artifacts: ocular artifacts. These artifacts originate from a non-cortical activity and contaminate the EEG recording. Thus, since the brain and eye activities have physiologically separate sources, the recorded EEG can be assumed to be superposition of the true cortical EEG and some portion of the OA signal:

$$EEG_{obs}(t) = EEG_{true}(t) + k \cdot OA(t) \quad (1)$$

where $EEG_{obs}$ is the observed contaminated EEG, $EEG_{true}$ is due to the cortical activity, and $k \cdot OA(t)$ is the propagated ocular artifact at the recording site. FIG. 4 is a graph showing an EEG time series corrupted by artifacts and broken down into coefficients of different time-frequency spans. FIG. 4.a) is such a recording, where the true cortical activity is superimposed to two large eye blinks.

It is of interest to estimate the ocular artifact based on the analysis of the observed signal $EEG_{obs}$. By subtracting the estimated OA from the observed EEG signal, a corrected EEG can be obtained, which minimizes the effect of the artifact and gives appropriate representation of the true cortical signal. This is actually achieved by denoising. In order to perform denoising and extract $EEG_{true}$, a time-frequency transform is first applied which decomposes the signal $EEG_{obs}$ into components that are localized in both the time and frequency domains. In the preferred embodiment, this decomposition is achieved using a Stationary (also called Over-complete or Redundant) Wavelet Transform (SWT).

Let w denote an SWT transform that decomposes a given signal x into a number of time-frequency spans. Each span contains a time series of wavelet coefficients describing the time evolution of the signal in a particular frequency band:

$$w:x \rightarrow \begin{cases} \{c_L^w \text{band}: [0, f_s/2^L] \\ d_L^w \text{band}: [f_s/2^L, f_s/2^{L-1}] \\ \vdots \\ d_k^w \text{band}: [f_s/2^{k-1}, f_s/2^k] \\ \vdots \\ d_1^w \text{band}: [f_s/4, f_s/2] \end{cases} \quad (2)$$

where $f_s$ corresponds to the sampling frequency.

Figure 3:
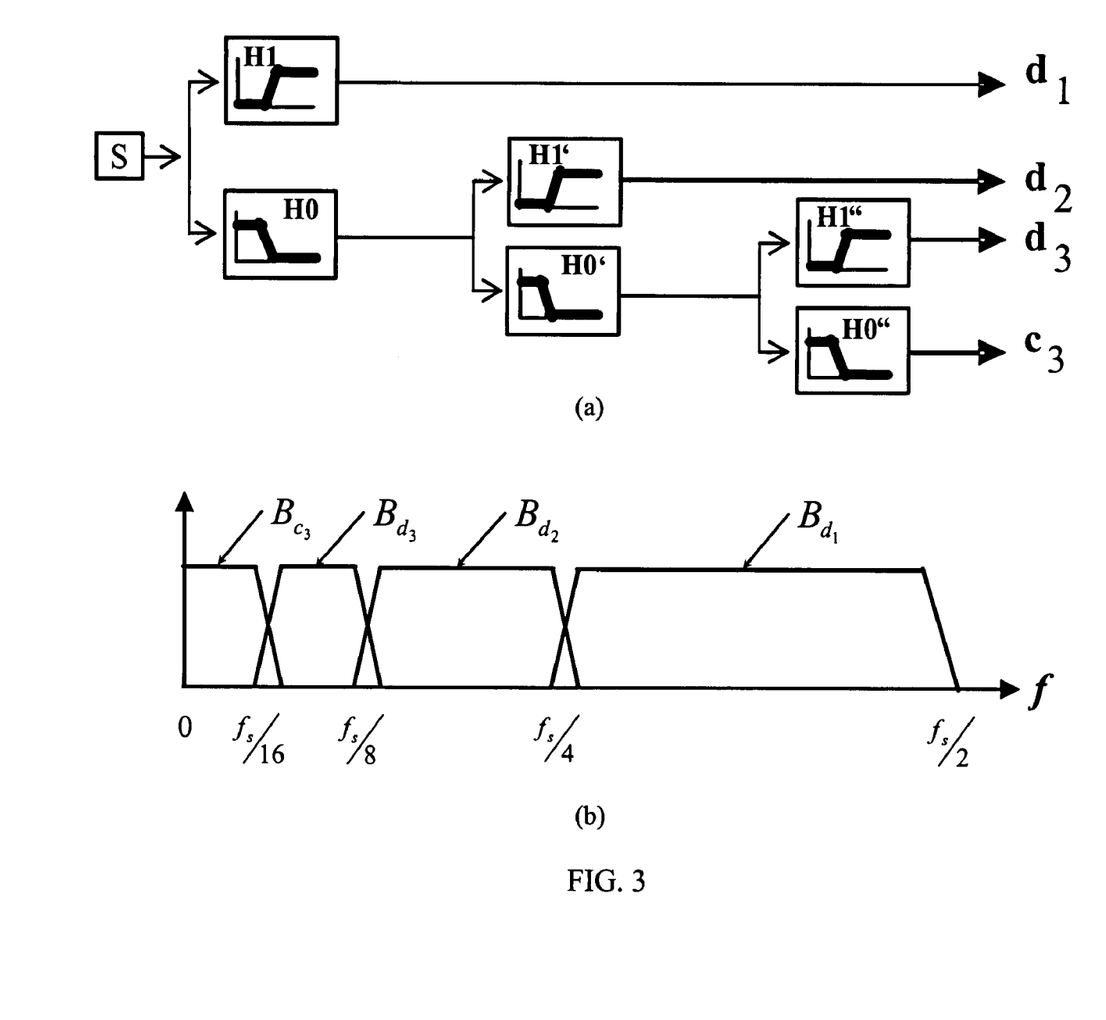

For instance, an L-level dyadic decomposition yields L+1 sets or time series of coefficients corresponding to a dyadic tiling of the frequency domain. FIG. 3.a) is a block diagram of stationary wavelet transform decomposition performed using filter banks; and b) is another graph showing dyadic tiling of a frequency space. FIG. 3.a) shows a SWT framework, where the wavelet decomposition is obtained through the use of filter banks based on 2 FIR filters, $H_0$ (low pass) and $H_1$ (high pass). The characteristic of the coefficient sets $\{c_L\}$ and $\{d_k\}_{k=1,\ldots,L}$ depends on the wavelet filters $H_0$ and $H_1$ associated to the transform w. In addition, filter coefficients of the filters $H_0'$, $H_1'$, $H_0''$ and $H_1''$ are simply derived by upsampling the coefficients of the filters $H_0$ and $H_1$. FIG. 3.b) shows the corresponding dyadic frequency bands of decomposition.

FIG. 4 also shows a 5-level SWT transform applied to the observed EEG corrupted by two large eye blinks and sampled at 128 Hz. As a result, wavelet coefficients in 6 time-frequency spans are obtained. Each coefficient represents the activity of the observed EEG at that particular point in time and in the frequency band which is characteristic for that particular span.

The pre-calculated threshold values are then applied to coefficients in each span. The thresholds of the time-frequency spans $\{d_k\}_{k=1,\ldots,L}$ are defined by two bounds: $T_{k,max}$ and $T_{k,min}$. The thresholds of the time-frequency span $\{c_L\}$ are also defined by two bounds: $T_{L+1,max}$ and $T_{L+1,min}$. Any coefficient that exceeds these bounds defined by the thresholds is then replaced with a replacement value. In this example, the replacement value is 0. The so-called denoised time-frequency spans are then used to reconstruct a time series representing the denoised EEG. This reconstruction is done by applying the inverse SWT transform.

Obviously, this method relies on the appropriate selection of the thresholds $\{T_{k,min}, T_{k,max}\}_{k=1,\ldots,L+1}$. Usually, it is desired to preserve as much of the $EEG_{true}$ information as possible. Hence, if the EEG is free of artifacts, it is necessary to ensure that the thresholds do not affect time-frequency coefficients corresponding to $EEG_{true}$. In case of spontaneous EEG signal, the signal of interest is noise-like. No clear patterns can be observed within it, nor can it simply be correlated to the particular underlying events with its waveshape. Also, EEG amplitude histograms in conscious subjects have a nearly Gaussian distribution. Furthermore, although the variance of the EEG signal can significantly change from one second to another, this variation is small in comparison with the variance of the signal corrupted by artifacts. Thus, the EEG signal in conscious subjects can be considered quasistationary. Therefore, the distribution of the time-frequency span coefficients of artifact-free EEGs can be considered to be Gaussian. Hence, the thresholds could be estimated by simple statistical analysis of the artifact-free EEGs.

For this purpose, the database of N artifact-free EEGs is analyzed using the previously selected SWT decomposition. For every EEG from the database, the maximum absolute value $M_k$ of wavelet coefficients is calculated for each time-frequency span k(k=1 ... L+1) of the L-level SWT decomposition. In order to ensure that a very small percentage of coefficients corresponding to the artifact-free EEGs are affected by the thresholding process, the thresholds are derived according to the following equations:

$$\begin{cases} T_{k,max} = \overline{M_k} + 2 \cdot \text{std}(M_k) \\ T_{k,min} = -T_{k,max} \end{cases}, k = 1 \ldots L+1 \quad (3)$$

where $\overline{M_k}$ and $\text{std}(M_k)$ are, respectively, the mean and standard deviation of the set $\{M_k\}$, k=1 ... L+1.

Note that each set $\{M_k\}$ has N elements corresponding to the number of artifact-free EEGs in the database.

Other values can be chosen for the thresholds, such as 0, 1, or 3 instead of 2 standard deviations as in (3). In addition, one can set the thresholds $T_{k,max}$ to be equal to 2 or 3 standard deviations of the wavelet coefficients in the time-frequency spans k obtained from the SWT decomposition of the artifact-free database. This would mean that only 5% and 1%, respectively, of the coefficients corresponding to the artifact-free EEGs would be affected by denoising. Thus, larger bounds result in a more conservative denoising design since more of the $EEG_{true}$ coefficients are unaffected. However, this also means that more of the artifactual coefficients remain in the denoised EEG. It is also interesting to notice that the thresholds do not depend on a characterization of the artifactual coefficients.

Note that each time-frequency span of the proposed denoising method comprises the same number of coefficients due to the use of the SWT. This allows for better time localization of artifacts in the time-frequency spans corresponding to lower frequencies. Also, this provides the same number of coefficients for deriving the thresholds in all time-frequency spans. (For non-redundant wavelet transforms, the number of coefficients dyadically decreases for time-frequency spans with decreasing frequencies.)

Figure 5:
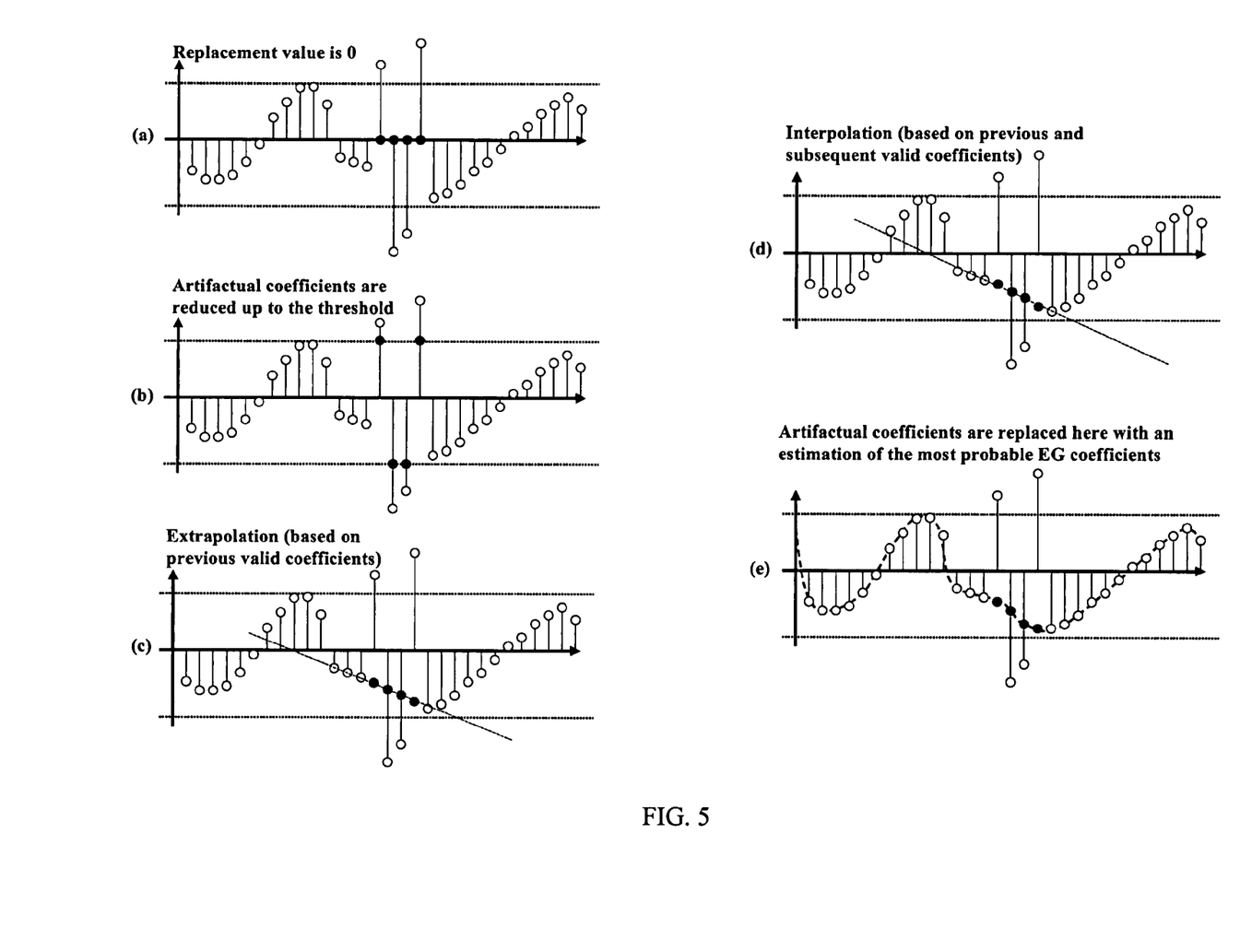
FIG. 5 are graphs showing different strategies that can be implemented when choosing the replacement values of the thresholded coefficients.

FIG. 5 are graphs showing different strategies that can be implemented when choosing coefficients and the replacement values of the thresholded coefficients. The main task of thresholds is to separate the $EEG_{true}$ coefficients from the OA coefficients. Once this characterization of the coefficients is made, appropriate steps can be taken in order to denoise the observed EEG. In FIG. 5.a), each artifactual coefficient is replaced by 0. This denoising strategy is appropriate for the denoising of EEG. However, other strategies can be envisaged according to the type of electrograms. For instance, in FIG. 5.b) artifactual coefficients can be reduced to the closest threshold value. Other strategies consist in replacing the artifactual coefficients by values derived based on the valid coefficients immediately in the vicinity of the artifactual coefficients. Any type of interpolation or extrapolation can be made. FIGS. 5.c-e) show more complex prediction techniques based on electrogram modeling can also be implemented.

Figure 6:
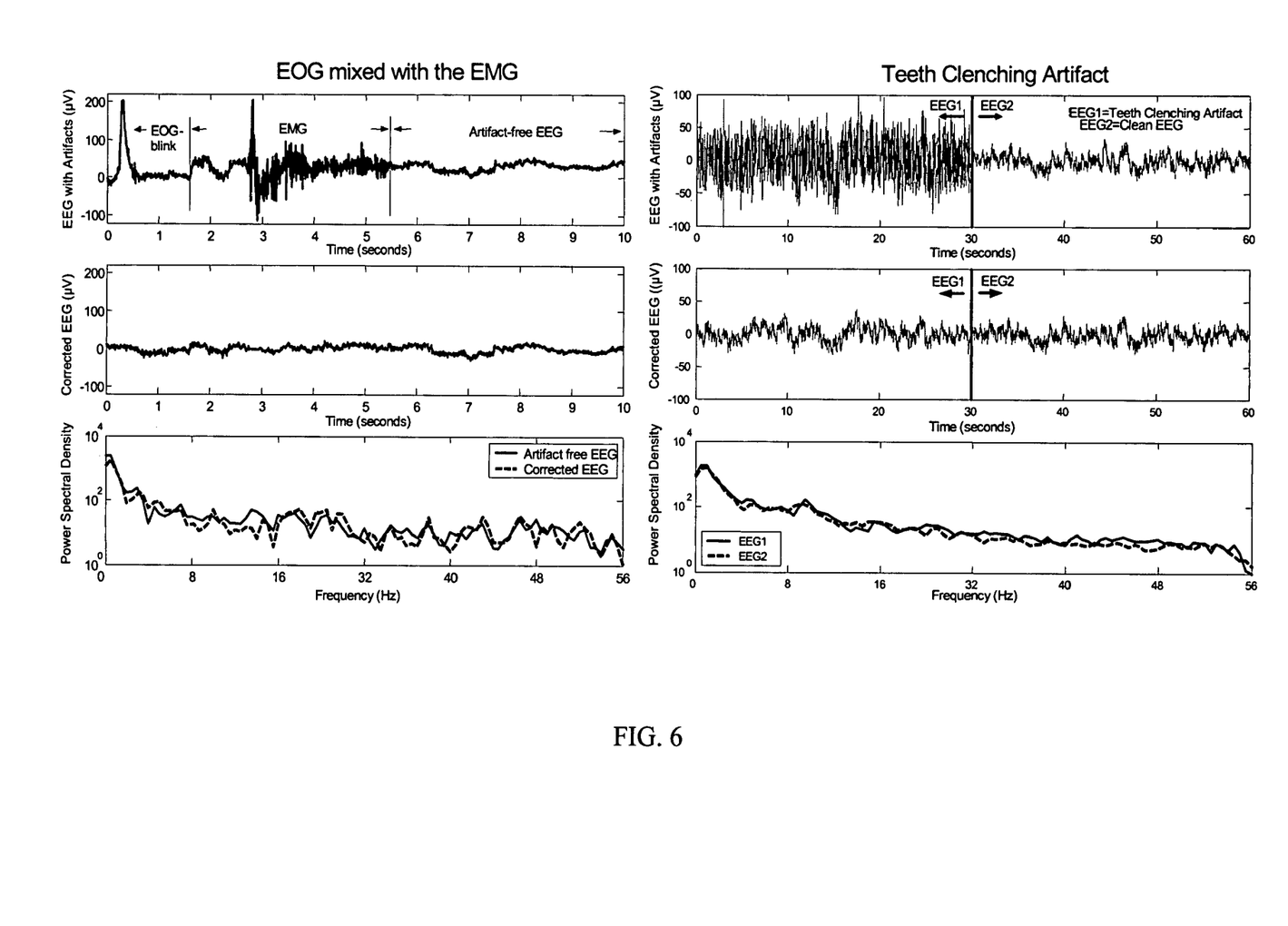
FIG. 6 are graphs illustrating the results of the denoising technique of one of the embodiments of the present invention when applied to EEGs which are simultaneously perturbated by a variety of artifacts.

The present invention has been illustrated for removal of Ocular Artifacts (OAs) from the Electroencephalogram (EEG). The same method can be successfully used to simultaneously, with OAs, remove the additional artifacts embedded within the EEG, such as head movement and muscle activity artifacts. The nature of ECG artifacts makes them suitable candidates for being removed from the EEG by this method as well. FIG. 6 are graphs illustrating the results of the denoising technique of one of the embodiments of the present invention when applied to EEGs which are simultaneously perturbated by a variety of artifacts. In this case, the thresholds were derived from the 60-second artifact-free EEG acquired from the same subject. The analysis was performed using a 5-level SWT decomposition with Coiflet 3 wavelet filter. This filter was chosen since its shape resembles eye blinks, which leads to good time localization of these artifacts. The same filter has proven to work well for other types of artifacts as well. Note that, for different type of artifacts, the actual denoising affects the coefficients in different frequency bands.

Furthermore, the same method can be applied to a wide variety of electrograms and artifacts, as long as the EG signal of interest and artifacts can be separated in transform domain in at least some of the time-frequency spans of decomposition. By thresholding coefficients in these transform spans, the artifact can be at least reduced.

For example, in case of ECG signal of interest, the proposed technique can be successfully used for both lower and higher frequency artifacts, including various types of noise. However, since ECG shape is well defined, a good strategy for denoising is to calculate the replacement values of the thresholded coefficients based on the valid ECG coefficients immediately in the vicinity of the artifactual coefficients. Interpolation or extrapolation can be implemented, or even better, more complex prediction techniques based on ECG modeling. This is illustrated in FIGS. 5 c-e). In addition, different replacement values can be used for different time-frequency spans.

In case of EMG signal, which is less coherent and smooth than ECG signal, similar strategies to those described for EEG signal can be used.

Also, if EOG is signal of interest, previously described EEG denoising produces both the denoised EEG signal and artifactual signal, the later mainly comprising of EOG signal in case of conscious subjects. A secondary denoising can then be applied to the artifactual signal to further separate other artifacts from EOG of interest. This can be very useful in applications that use both the EEG and EOG signals since, by deriving the EOG from the EEG signal, the number of required channels can be reduced. Also, EOG signals recorded from electrodes placed around subjects' eyes can also be easily denoised by strategies similar to those described, e.g., for ECG.

In addition, the presented method is simple and computationally efficient. It can also be easily automated and implemented in real time. For example, in case of EEG signal, an analysis epoch can be as short as 0.5 seconds for a sampling frequency of 128 Hz. The length of epoch can be even shorter for higher sampling frequencies. Also, as previously mentioned, the reference artifact-free EEG signal can be very short, e.g., less than 60 seconds in applications involving EEG analysis in conscious subjects. Furthermore, when computational complexity is not of a concern, higher levels of decomposition can produce even better results.

Finally, it can be of importance to keep track of the number of artifactual coefficients detected and replaced by the denoising function. If this number is high, it is probable that the denoised electrogram might not carry enough meaningful information. In this case, it could be appropriate to discard the current EG from any further analysis.

Figure 1:
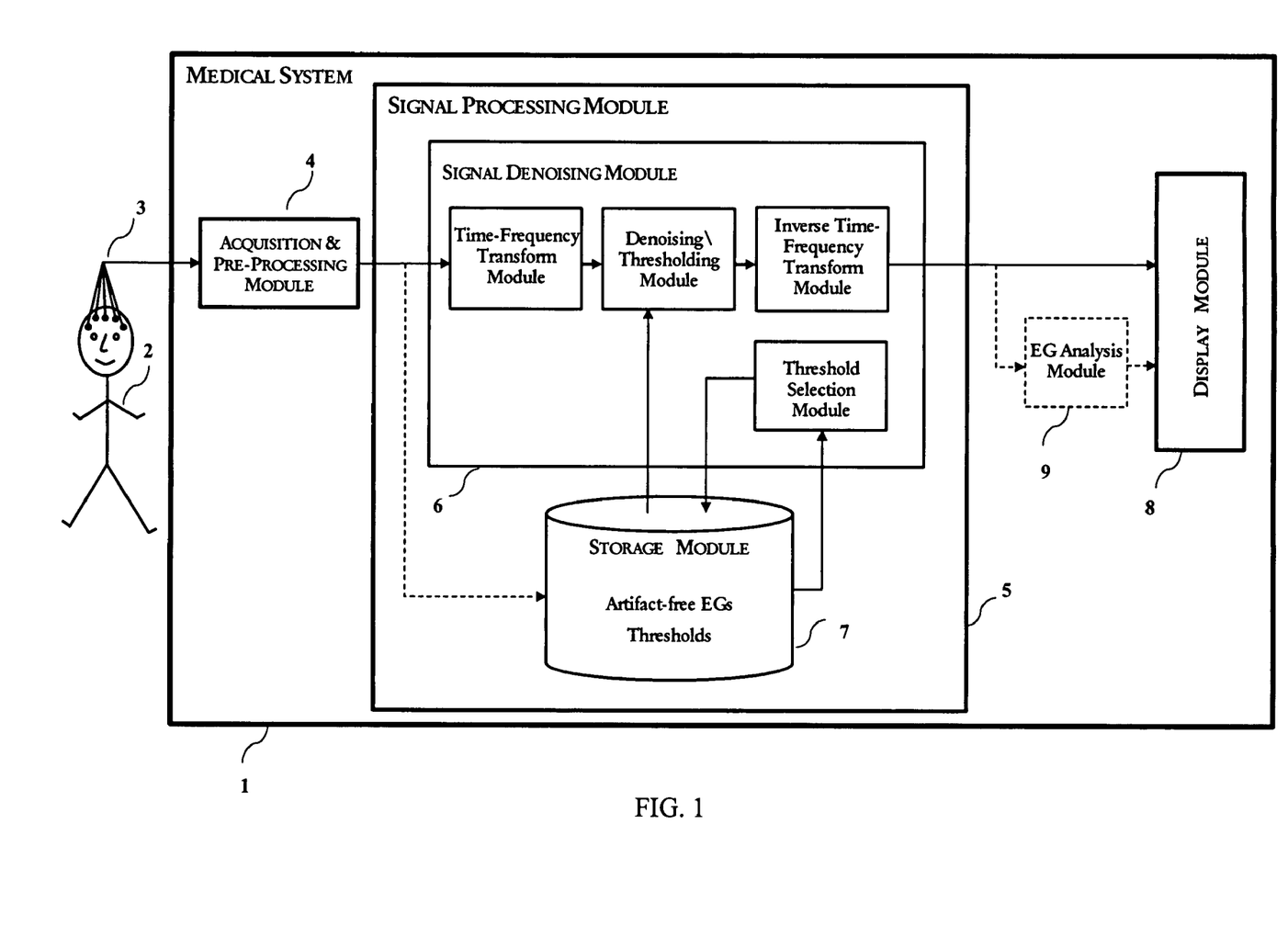
FIG. 1 is a block diagram of a medical system comprising one embodiment of the method of the present invention.

The various embodiments of the present invention can further be described with a more detailed description of FIGS. 1-11 of this application. FIG. 1 is a block diagram of a medical system comprising one embodiment of the method of the present invention. In FIG. 1 a medical system 1 is connected to a subject 2 via an array of sensors 3. This array involves using at least one sensor to measure subject's EG signals of interest over a period of time. EG signals (such as EEG, ECG, EMG, EOG, pulse oximetry signal and other electrograms) can be obtained by any method know in the art, or subsequently developed by those skilled in the art to detect these types of signals. Sensors include but are not limited to electrochemical pads (such as various disposable pre-gelled electrodes), other conductive electrodes that require the use of various conductive pastes\gels (such as gold cup electrodes), electromechanical electrodes (such as various dry electrodes that mechanically abrade the skin), electromechanical transducers such as pressure sensors (blood pressure cuffs, etc.), electro-optical devices such light transducers for pulse oximetry, mass spectrometers for capnography and gas analysis, and magnetic sensors. These sensors may be placed at one or several locations on the subject's scalp or body. In addition to these surface sensors, other sensors may be implanted. For example, electrodes can be placed under subject's skin such as various needle electrodes, or even deeper, such as so-called epidural and subdural electrodes placed directly on the surface of the brain or deep in the brain, and epidural spinal electrodes. Various implanted sensors may also use telemetry to provide receiving of EG signals by a medical system 1.

The EG is thus first acquired via an acquisition & pre-processing module 4, which comprises an amplifier, a set of low pass and high pass filters, and a digitizer that transforms the analog EG signal received from an array of sensors 3 into a digital EG signal. The digital EG signal is then stored into a buffer memory, e.g., within the acquisition & pre-processing module 4. The signal can be sampled in any sampling frequency, however, it is preferable to use higher sampling frequencies. Preferably, the sampling frequency is greater than 60 Hz, more preferably the sampling frequency is greater than 120 Hz, even more preferably, the sampling frequency is greater than 240 Hz, still even more preferably the sampling frequency is greater than 480 Hz, and most preferably the sampling frequency is greater than 960 Hz. Most preferably the sampling frequency is in the form of some power of 2.

Various computers, processors, transceivers, receivers, transmitters and the like can be used in the various embodiments of the present invention. The various methods and computer programs of the present invention may be resident on a computer, processor (and their memories), or other electronic data media, which are used to perform these complex functions. The signals can be transmitted and/or received by either telemetry or by wire (through a tethered system).

The signal processing module 5 of the present invention has a task to remove contaminating artifacts from the EG signal. Thus, the signal processing module outputs a time series corresponding to the denoised electrogram. The signal processing module comprises two main elements: a signal denoising module 6 and a storage module 7. This information is then either displayed directly by the display module 8, or processed by a secondary EG analysis module 9 to extract relevant clinical information. The signal denoising module 6 is an algorithm dedicated to the task of removing the contaminating artifacts from the digitized EG.

Figure 7:
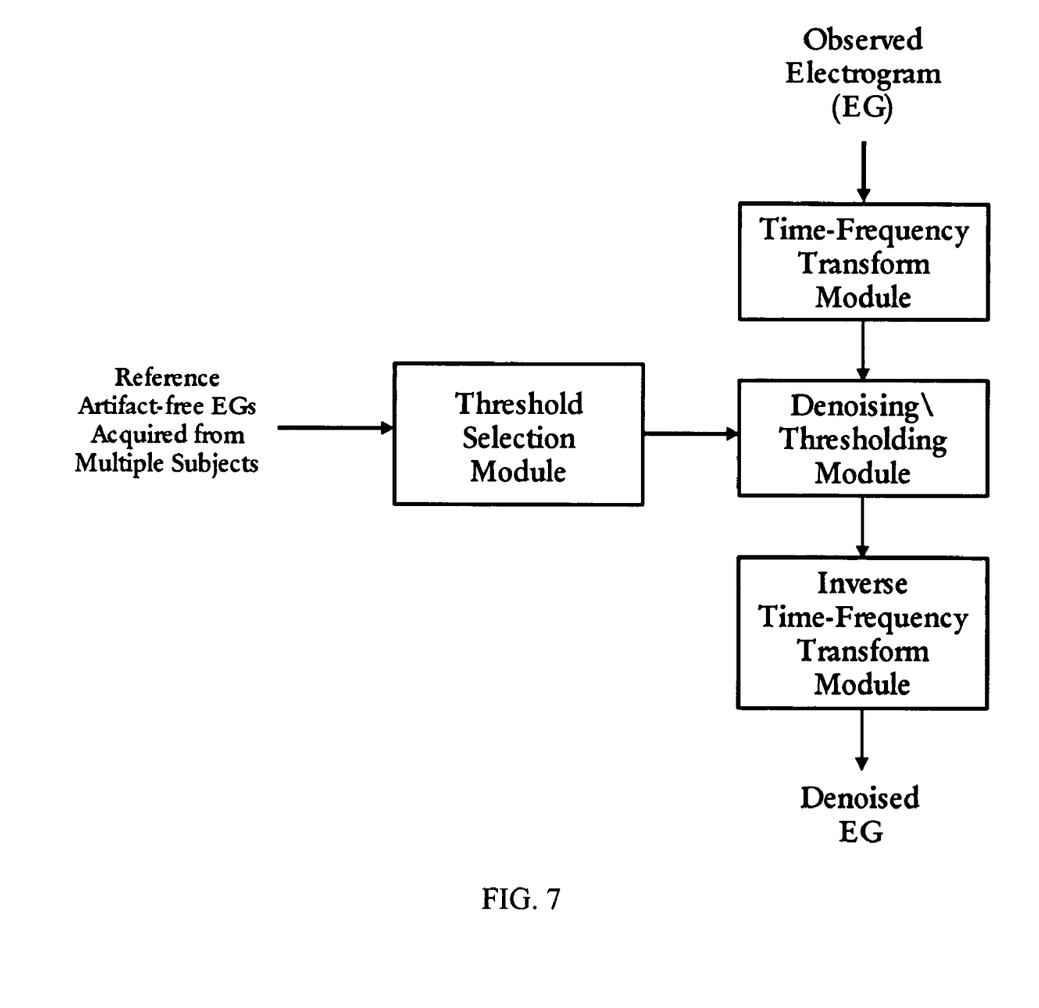
FIG. 7 is a block diagram depicting the artifact removal method of various embodiments of the present invention by using a signal processing module according to another embodiment of the present invention.

FIG. 7 is a block diagram depicting the artifact removal method of various embodiments of the present invention by using a signal processing module according to another embodiment of the present invention. In this embodiment, the software algorithm comprises two distinct functions: an initialization function 10 and a main denoising function 11, as depicted by the flow diagram of FIG. 8.

Figure 8:
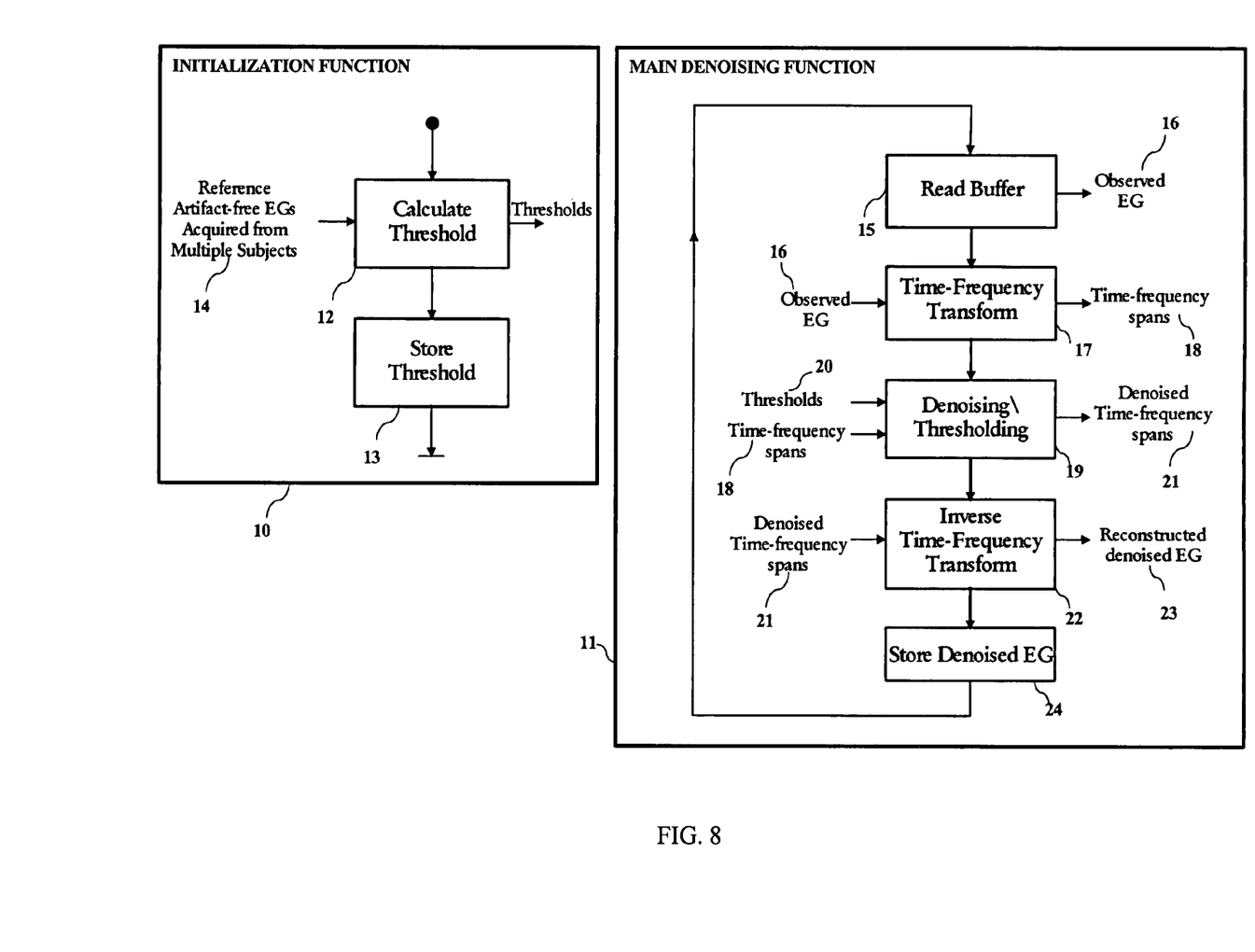
FIG. 8 is a flow diagram of one embodiment of the signal denoising module software algorithm.

The main task of the initialization function 10 is to calculate 12 and store the thresholds 13. This is achieved by analyzing a set of reference artifact-free EGs 14 acquired in a previous session from multiple subjects. Each artifact-free EG is first decomposed using a pre-selected L-level SWT transform w. For each time-frequency span k resulting from this decomposition, two threshold values $T_{k,max}$ and $T_{k,min}$ corresponding to a minimum and a maximum bound are derived. In the preferred embodiment, these two values are calculated as in (3), in which case, most of the coefficients in each span are contained within the threshold bounds. Other formulae can be used to derive these bounds using a wide variety of statistical functions to characterize the coefficient distribution in each of the decomposition spans.

Once the thresholds are calculated, they are stored in the storage module 7. In this embodiment, the initialization function 10 is called only once during the first access to the signal processing module 5. In this same embodiment, the EG is acquired in real-time from a subject. Each time when the acquisition & pre-processing module 4 contains the entire observed EG, a call to the main denoising function 11 is made. The function will then read 15 the buffer memory which contains the observed EG. The observed EG time series 16 is then transformed 17 using the selected L-level SWT transform to yield L+1 time-frequency spans 18. Each of these spans contains a time series of coefficients $\{c_L\}$ and $\{d_k\}_{k=1,\ldots,L}$. Each time-frequency span 18 is then input to the denoising\thresholding function 19 which uses the threshold values 20 previously calculated and stored by the initialization function 10. The coefficients in each of the time-frequency spans are then compared to the threshold values. If the coefficient is greater than $T_{k,max}$ or less than $T_{k,min}$, it is substituted by a replacement value. In this embodiment the replacement value is 0.

Once the comparison and replacement are performed for each coefficient of each time-frequency span, the denoised time-frequency spans 21 are input to the inverse time-frequency transform function 22 which reconstructs the denoised EG. This denoised EG 23 is finally stored 24 in order to be processed by the EG analysis module 9 of the medical system. The main denoising function 11 will then wait for the next cycle, i.e., the next observed EG.

Figure 9:
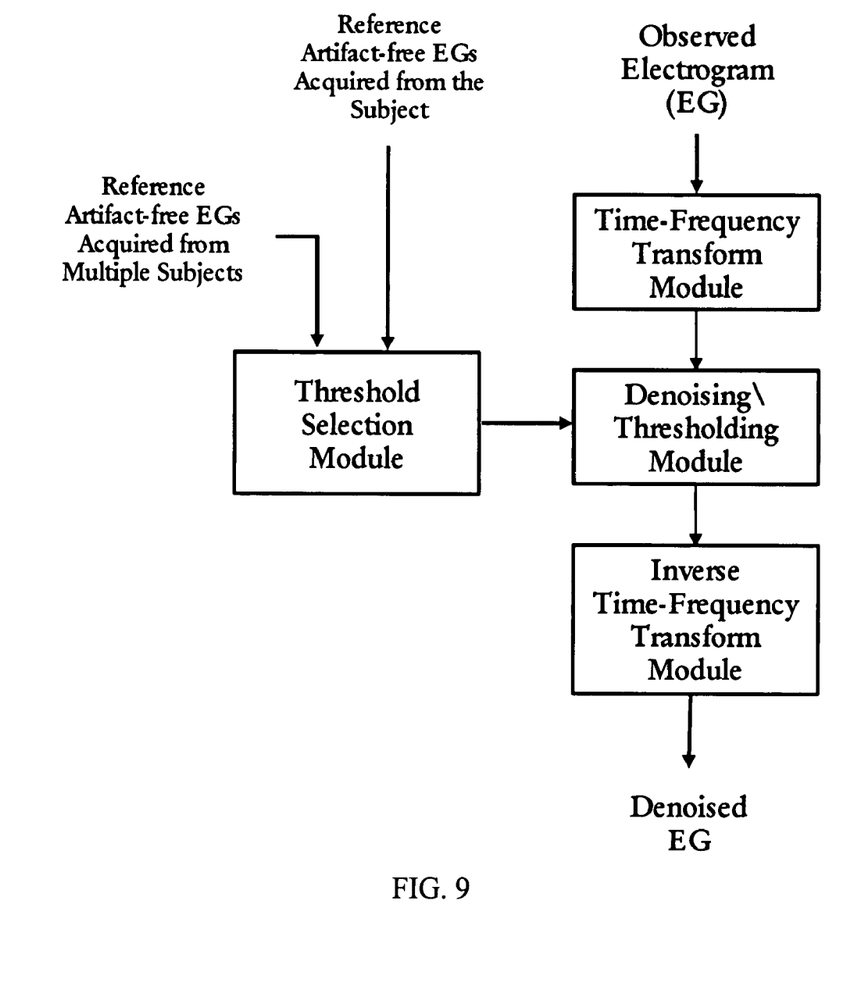
FIG. 9 is a block diagram depicting one embodiment of the artifact removal process of the present invention by a signal processing module according to various other embodiments of the present invention.
Figure 10:
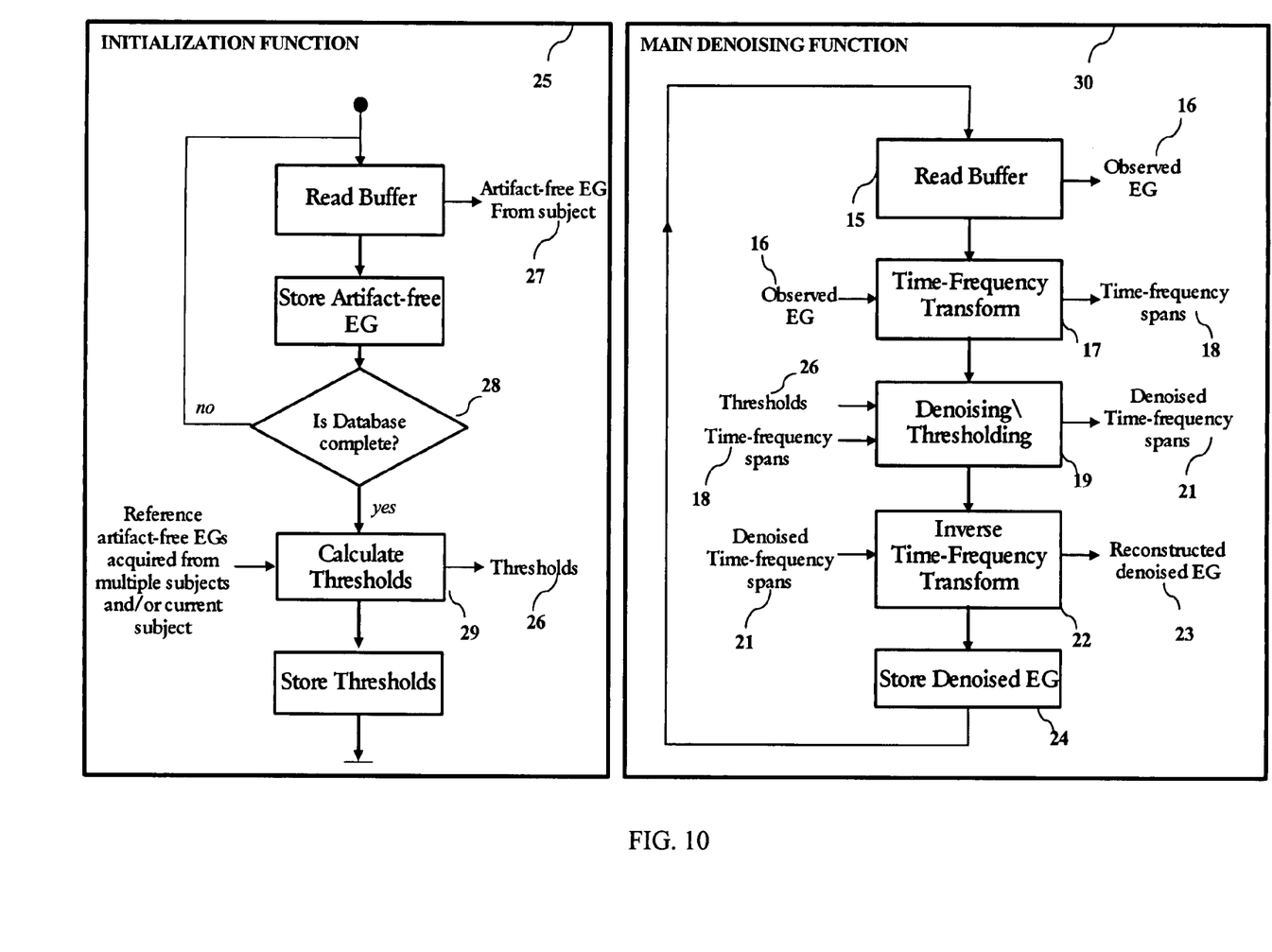
FIG. 10 is a flow diagram of another embodiment of the signal denoising module software algorithm.
Figure 11:
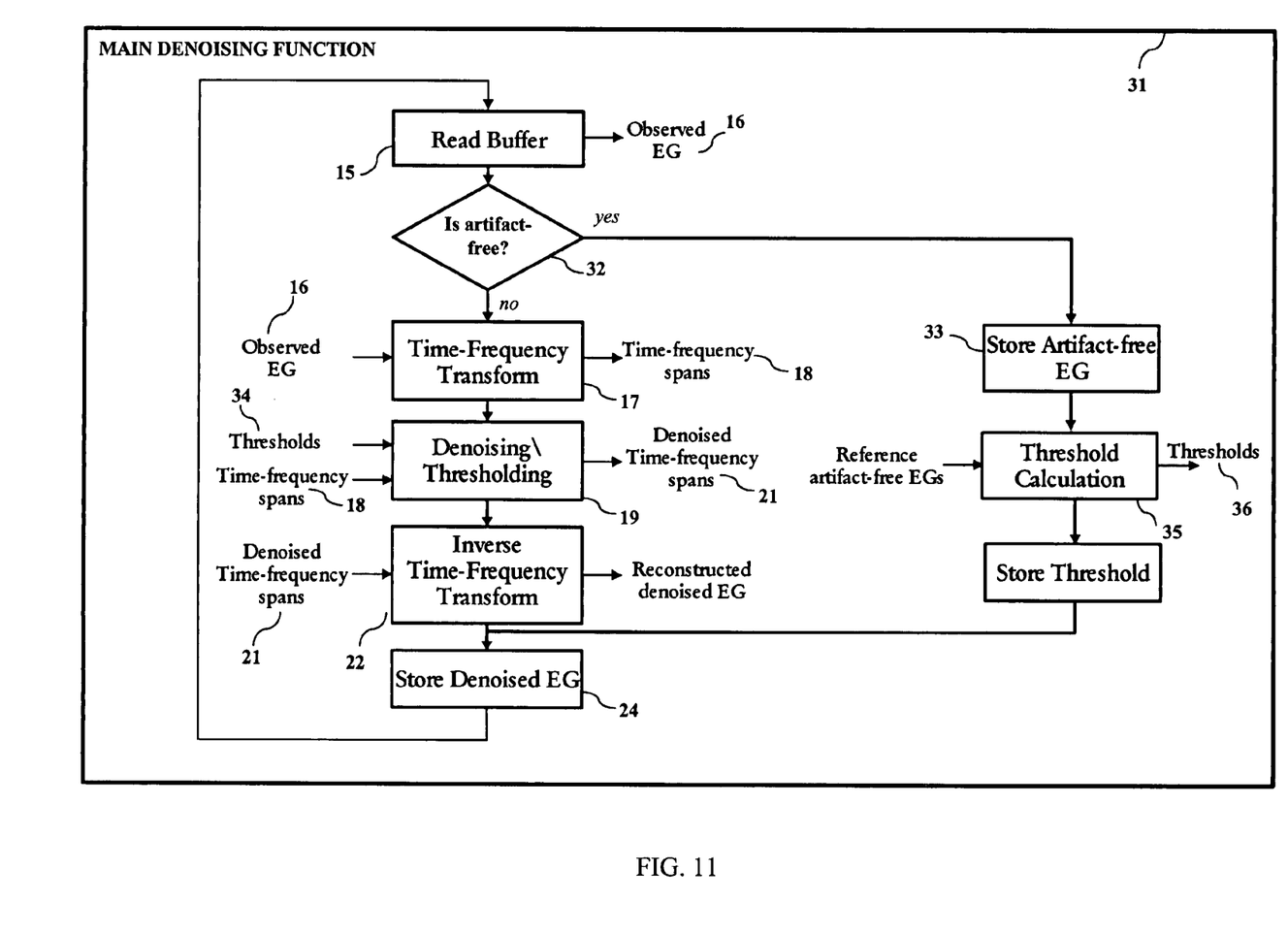
FIG. 11 is a flow diagram of still another embodiment of the signal denoising module software algorithm.

Two other embodiments of the present invention are shown in FIG. 9, with the corresponding software algorithms depicted by flowcharts presented in FIGS. 10 and 11, respectively.

FIG. 10 is a flow diagram of one of these embodiments of the signal denoising module software algorithm. In FIG. 10, the initialization function 25 is modified in order to allow the system to derive thresholds 26 specifically based on the subject's own EGs. In the first step, the algorithm builds a database of artifact-free EGs 27 from the subject. In order to achieve this, it is necessary that the subject is asked to minimize the source of the artifacts. In case of EEG signals and their denoising, this calibration procedure can be rather short (less than 1 minute of artifact-free EEGs is usually sufficient), while the subject is asked to be still with his or her eyes shut. Once the database is complete and its contents are deemed valid 28, the subject's artifact-free EGs are used to calculate 29 the thresholds 26 in a similar way as in the previous embodiment. The main denoising function 30 operates in a similar fashion as in the previously described embodiment.

FIG. 11 is a flow diagram of still another embodiment of the signal denoising module software algorithm. The initialization function of the two previously described embodiments 10 and 25 can be used to derive the initial thresholds. Once the main denoising function 31 is looping, a classification function 32 determines whether the current observed EG contains artifacts. If it does, the EG is input to the time-frequency transform 17. In this case, the algorithm carries out the same denoising technique as previously described. If the EG is artifact-free then no denoising is needed, and it can be used to calculate new thresholds 34. In this case, the observed EG is appended to the current database 33 of artifact-free EGs, and the thresholds are updated 36. Note that in this embodiment, the time-frequency transform used in the threshold calculation function 35 and in the denoising path 17 is the same. Hence this time-frequency transform can also be carried out before the classification function.

The above described embodiment can be utilized in applications which are interested in EGs corresponding to different physiological states of a subject, where statistics of an EG of interest can significantly change over time. In this case, the method is able to adapt the threshold values according to the subject's current state. This embodiment can further be utilized in applications that are interested in EGs that might carry some pathological patterns resembling artifacts. In this case, the classifier function 32 is programmed to make distinction between these artifact-like shapes and real artifacts.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A system for removing artifacts from an observed electrogram of a subject in order to produce a denoised electrogram, given a time-frequency transform, and given a database of reference electrograms, each said reference electrogram being free of said artifacts, and each said reference electrogram having been acquired from individuals other than said subject, said system comprising:
   a. a sensor for acquiring the electrogram of said subject to complement said database of reference electrograms, and for producing said observed electrogram; and
   b. a digital signal processor for:
      i. applying said time-frequency transform to said reference electrograms to produce a plurality of reference coefficient sets, each said reference coefficient set corresponding to a respective time-frequency span;
      ii. calculating a threshold for each said time-frequency span based on a corresponding reference coefficient set;
      iii. applying said time-frequency transform to said observed electrogram to produce a plurality of observed coefficient sets, each said observed coefficient set corresponding to a respective time-frequency span;
      iv. comparing each coefficient of each said observed coefficient set with the corresponding threshold for a respective time-frequency span;
      v. replacing every large coefficient of each said observed coefficient set which is above the respective threshold for the corresponding time-frequency span with a replacement value in order to produce denoised observed coefficient sets; and
      vi. applying the inverse transform of said time-frequency transform to said denoised observed coefficient sets to reconstruct the denoised electrogram.

2. The system of claim 1, wherein said electrograms are electroencephalograms.

3. The system of claim 1, wherein said time-frequency transform is a wavelet transform.

4. The system of claim 1, wherein said threshold comprises two values which define a maximum coefficient bound and a minimum coefficient bound, and wherein said maximum and minimum coefficient bounds are defined such that most of coefficients of said reference coefficient sets are contained within these bounds.

5. The method of claim 1, wherein said replacement value is any number less than or equal to the threshold including 0.

6. The method of claim 1, wherein said replacement value is an estimation of the value of the coefficient being replaced, had the artifact never occurred.

7. A method for removing artifacts from an observed electrogram of a subject in order to provide a denoised electrogram, said method comprising:
   a. acquiring a plurality of reference electrograms, each said reference electrogram being free of said artifacts;
   b. selecting a time-frequency transform which, when applied to said reference electrograms yields a plurality of reference coefficient sets, each said reference coefficient set corresponding to a respective time-frequency span;
   c. selecting a threshold for each time-frequency span;
   d. acquiring an electrogram from said subject to produce said observed electrogram;
   e. applying said time-frequency transform to said observed electrogram to produce a plurality of observed coefficient sets, each said observed coefficient set corresponding to a respective time-frequency span;
   f. comparing each coefficient of each said observed coefficient set with the corresponding threshold for a respective time-frequency span; and
   g. replacing every large coefficient of each said observed coefficient set which is above exceeds the respective threshold for the corresponding time-frequency span with a replacement value in order to produce denoised observed coefficient sets.

8. The method of claim 7, wherein said electrograms are electroencephalograms.

9. The method of claim 7, wherein said time-frequency transform is a wavelet transform.

10. The method of claim 7, wherein said threshold comprises two values which define a maximum coefficient bound and a minimum coefficient bound, and wherein said maximum and minimum coefficient bounds are defined such that most of coefficients of said reference coefficient sets are contained within these bounds.

11. The method of claim 7, wherein said replacement value is any number less than or equal to the threshold, including 0.

12. The method of claim 7, wherein said replacement value is an estimation of the value of the coefficient being replaced, had the artifact never occurred.

13. The method of claim 7 wherein the inverse transform of said selected time-frequency transform is applied to said denoised observed coefficient sets to reconstruct a denoised electrogram.

14. The method of claim 7 wherein said time-frequency transform is a redundant wavelet transform.

15. The method of claim 7 wherein said time-frequency transform is a redundant wavelet packet transform.

16. The method of claim 7 wherein said reference electrograms are acquired from at least one individual other than said subject.

17. A method for extracting artifacts from an observed electrogram of a subject in order to provide an artifactual electrogram, said method comprising:
 a. acquiring a plurality of reference electrograms, each said reference electrogram being free of said artifacts;
 b. selecting a time-frequency transform which, when applied to said reference electrograms yields a plurality of reference coefficient sets, each said reference coefficient set corresponding to a respective time-frequency span;
 c. selecting a threshold for each time-frequency span;
 d. acquiring an electrogram from said subject to produce said observed electrogram;
 e. applying said time-frequency transform to said observed electrogram to produce a plurality of observed coefficient sets, each said observed coefficient set corresponding to a respective time-frequency span;
 f. comparing each coefficient of each said observed coefficient set with the corresponding threshold for a respective time-frequency span;
 g. replacing every small coefficient of each said observed coefficient set which is less than the respective threshold for the corresponding time-frequency span with a replacement value in order to produce artifactual observed coefficient sets; and
 h. applying the inverse transform of said selected time-frequency transform to said artifactual observed coefficient sets to reconstruct the artifactual electrogram.

18. The method of claim 17, wherein said electrograms are electroencephalograms.

19. The method of claim 17, wherein said time-frequency transform is a wavelet transform.

20. The method of claim 17, wherein said threshold comprises two values which define a maximum coefficient bound and a minimum coefficient bound, and wherein said maximum and minimum coefficient bounds are defined such that most of coefficients of said reference coefficient sets are contained within these bounds.

21. The method of claim 17, wherein said replacement value is 0.

22. The method of claim 17 wherein said reference electrograms are acquired from at least one individual other than said subject.

23. The method of claim 17 wherein said artifactual electrogram is subtracted from said observed electrogram in order to yield a denoised electrogram.

* * * * *